(12) United States Patent
Ito et al.

(10) Patent No.: US 9,648,879 B2
(45) Date of Patent: May 16, 2017

(54) CO-CRYSTAL AND METHOD FOR PRODUCING SAME

(71) Applicant: Nippon Soda Co., Ltd., Chiyoda-ku, Tokyo (JP)

(72) Inventors: Akihiko Ito, Joetsu (JP); Tomohiro Amano, Odawara (JP); Rieko Masaki, Makinohara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/034,981

(22) PCT Filed: Oct. 31, 2014

(86) PCT No.: PCT/JP2014/079081
§ 371 (c)(1),
(2) Date: May 6, 2016

(87) PCT Pub. No.: WO2015/072355
PCT Pub. Date: May 21, 2015

(65) Prior Publication Data
US 2016/0278380 A1    Sep. 29, 2016

(30) Foreign Application Priority Data
Nov. 13, 2013   (JP) ................................. 2013-235073

(51) Int. Cl.
*A01N 43/56* (2006.01)
*A01N 25/12* (2006.01)
*A01N 47/40* (2006.01)

(52) U.S. Cl.
CPC ............. *A01N 43/56* (2013.01); *A01N 25/12* (2013.01); *A01N 47/40* (2013.01)

(58) Field of Classification Search
CPC .................................................... A01N 43/56
USPC .......................................................... 514/341
See application file for complete search history.

(56) References Cited

U.S. PATENT DOCUMENTS

| | | | |
|---|---|---|---|
| 2007/0281929 A1 | 12/2007 | Amanokura et al. |
| 2009/0104145 A1 | 4/2009 | Hughes et al. |
| 2012/0252766 A1 | 10/2012 | Weiss et al. |
| 2012/0270904 A1 | 10/2012 | Weiss et al. |
| 2012/0283294 A1 | 11/2012 | Weiss et al. |
| 2016/0309718 A1 | 10/2016 | Yamamura |

FOREIGN PATENT DOCUMENTS

| | | |
|---|---|---|
| CN | 1988803 B | 9/2011 |
| CN | 102626071 A | 8/2012 |
| CN | 103283764 A | 9/2013 |
| JP | 2008-507582 A | 3/2008 |
| JP | 2013-510113 A | 3/2013 |
| WO | WO 2006/006596 A1 | 1/2006 |
| WO | WO 2006/068669 A1 | 6/2006 |
| WO | WO 2010/118833 A1 | 10/2010 |
| WO | WO 2011/054741 A2 | 5/2011 |
| WO | WO 2014/079820 A1 | 5/2014 |
| WO | WO 2015/093367 A1 | 6/2015 |

OTHER PUBLICATIONS

Zhao et al., Res. Chem. Intermed. (2013), vol. 39, pp. 3071-3088.*
International Search Report dated Jan. 13, 2015, in PCT/JP2014/079081.
Office Action dated Jun. 10, 2015, in TW 103137969.
Office Action dated Feb. 21, 2017, in JP 2015-547731, with English translation.
Supplementary European Search Report dated Mar. 15, 2017, in EP 14862188.1.
Ito, Akihiko, "Improvement of Active Ingredient Properties by Co-Crystallization," Summary of the 33$^{rd}$ Japan Agricultural Formulation and Application Symposium, Sep. 12-13, 2013, Shizuoka, published Aug. 15, 2013, p. 41, with English abstract.
Nauha et al., "Co-crystals of an agrochemical active—A pyridine-amine synthon for a thioamide group," Journal of Molecular Structure, Oct. 3, 2011, 1006(1):566-569.
Talley et al., "Atomic interactions of neonicotinoid agonists with AChBP: Molecular recognition of the distinctive electronegative pharmacophore," PNAS, May 27, 2008, 105(21):7606-7611.

* cited by examiner

*Primary Examiner* — Taofiq A Solola
(74) *Attorney, Agent, or Firm* — Foley & Lardner LLP (57) ABSTRACT

A co-crystal composed of a diamide-based insecticidal-active ingredient and a neonicotinoid-based insecticidal-active ingredient is provided as a co-crystal which exhibits excellent insecticidal effects over a long period of time while reducing the occurrence of chemical damage on useful plants. The co-crystal is obtained by a method including heating and stirring of a suspension obtained by suspending the diamide-based insecticidal-active ingredient and the neonicotinoid-based insecticidal-active ingredient in a solvent such as water.

9 Claims, 5 Drawing Sheets

CO-CRYSTAL AND METHOD FOR PRODUCING SAME

TECHNICAL FIELD

The present invention relates to a novel co-crystal consisting of a diamide-based insecticidal-active ingredient and a neonicotinoid-based insecticidal ingredient, a method for producing the same, and an agrochemical composition containing the same.

The present invention is a National Stage application of PCT/JP2014/079081, filed Oct. 31, 2014, which claims priority on the basis of Japanese Patent Application No. 2013-235073 filed in Japan on Nov. 13, 2013, the contents of which are incorporated herein by reference.

BACKGROUND OF THE INVENTION

Active compounds contained in agrochemicals such as insecticides, acaricides, fungicides, or herbicides, or in agents for controlling wood-destroying organisms such as termites are required to appropriately control elution thereof in order to maintain effects thereof or to reduce phytotoxicity in plants or toxicity in humans and animals.

There have been attempts to formulate active compounds having low water solubility so as to increase elution thereof. In contrast, there have been attempts to formulate active compounds having high water solubility so as to reduce the elution rate thereof.

Neonicotinoid-based compounds belong to a compound group which exhibits an insecticidal effect as a nicotinic acetylcholine receptor agonist or antagonist. Many compounds included therein have high water solubility. Therefore, reducing the phytotoxicity caused by application at a high concentration and maintaining effects over a long period of time by reducing the elution rate or the hoarding amount have been considered. As a method for adjusting the elution rate, a compound in which the neonicotinoid-based compound is included in a multimolecular host compound has been proposed (Patent Document 2). In addition, there is a case in which a change in elution properties is caused by formation of a co-crystal. For example, Patent Document 1 discloses a co-crystal composed of imidacloprid, which is an insecticide, and oxalic acid.

DOCUMENTS OF RELATED ART

Patent Documents

Patent Document 1: WO 2010/118833
Patent Document 2: WO 2006/006596

SUMMARY OF THE INVENTION

Problems to be Solved by the Invention

An object of the present invention is to provide an insecticidal composition or the like which exhibits excellent insecticidal effects over a long period of time by adequately controlling the water solubility of an insecticidal-active compound, and in which there is no concern of phytotoxicity on useful plants or the like.

Means to Solve the Problems

The present inventors have conducted extensive studies in order to solve the above-described problems, and as a result, they have found that a neonicotinoid-based insecticidal-active ingredient and a diamide-based insecticidal-active ingredient form a co-crystal, and the use of the co-crystal is effective for reducing elution of the neonicotinoid-based insecticidal ingredient having high water solubility, as a result of which the present invention has been completed.

The present invention relates to the following.

(1) A co-crystal consisting of a diamide-based insecticidal-active ingredient and a neonicotinoid-based insecticidal-active ingredient.

(2) The co-crystal according to (1), wherein the molar ratio of the diamide-based insecticidal-active ingredient to the neonicotinoid-based insecticidal-active ingredient is 0.3 to 3.

(3) The co-crystal according to (1) or (2), wherein the neonicotinoid-based insecticidal-active ingredient is a compound of Formula (1).

[Chemical formula 1]

(In the formula,
$R^1$ represents $CHR^{11}R^{12}$, $NR^{11}R^{12}$, or $SR^{12}$,
$R^{11}$ and $R^{12}$ each independently represents a hydrogen atom, or a C1-2 alkyl group,
$R^2$ represents a halogen atom, a cyano group, a nitro group, or an unsubstituted or substituted C1-6 acyl group,
$R^3$ represents a hydrogen atom, a C1-6 alkyl group, a C1-6 haloalkyl group, or a C3-6 cycloalkyl group,
$R^4$ represents a hydrogen atom or a methyl group;
Het represents an unsubstituted or substituted 5- to 6-membered heterocyclic group;
A represents N or $CR^{13}$, in which $R^{13}$ represents a hydrogen atom or a C1-2 alkyl group, and
any one of $R^2$ and $R^{13}$ with $R^1$, and, $R^{12}$ with $R^3$, may each independently form a 5- to 6-membered heterocyclic group).

(4) The co-crystal according to (1) or (2), wherein the neonicotinoid-based insecticidal-active ingredient is one selected from the group consisting of imidacloprid, acetamiprid, thiamethoxam, clothianidin, thiacloprid, nitenpyram, N-[3-[(6-chloro-3-pyridinyl)methyl]-2(3H)-thiazolylidene]-2,2,2-trifluoroacetamide, and N-[1-[(6-chloro-3-pyridinyl)methyl]-2(1H)-pyridinelidene]-2,2,2-trifluoroacetamide.

(5) The co-crystal according to (1) or (2), wherein the diamide-based insecticidal-active ingredient is a compound of Formula (2).

[Chemical formula 2]

(In the formula,
Q represents $CR^{14}$ or a nitrogen atom,
$R^{14}$ represents a hydrogen atom, an unsubstituted or substituted C1-6 alkyl group, or an unsubstituted or substituted C2-6 alkenyl group, $R^5$ and $R^8$ each independently represents a halogen atom, a cyano group, a nitro group, an unsubstituted or substituted C1-6 alkyl group, an unsubstituted or substituted C2-6 alkenyl group, or an unsubstituted or substituted C2-6 alkynyl group, n1 represents 0 or an integer of 1 to 3;

n2 represents 0 or an integer of 1 to 4;

$R^6$ represents a halogen atom, a cyano group, a nitro group, or an unsubstituted or substituted C1-6 acyl group, $R^7$ represents a hydrogen atom, an unsubstituted or substituted C1-6 alkylthio group, or an unsubstituted or substituted C1-6 alkylsulfinyl group, $R^9$ represents an unsubstituted or substituted C1-6 alkyl group, an unsubstituted or substituted C2-6 alkenyl group, or an unsubstituted or substituted C2-6 alkynyl group).

(6) The co-crystal according to (1) or (2), wherein the diamide-based insecticidal-active ingredient is cyantraniliprole, chlorantraniliprole, or cyclaniliprole.

(7) A method for producing the co-crystal of any one of (1) to (6), including: suspending the diamide-based insecticidal-active ingredient and the neonicotinoid-based insecticidal-active ingredient in a solvent to obtain a suspension, and heating and stirring the suspension.

(8) The method for producing the co-crystal according to (7), wherein the heating temperature is higher than or equal to 40° C. but lower than or equal to the boiling point of the solvent.

(9) The method for producing the co-crystal according to (8), wherein the heating temperature is higher than or equal to 60° C. but lower than or equal to the boiling point of the solvent.

(10) The method for producing the co-crystal according to any one of (7) to (9), wherein the solvent is water.

(11) An agrochemical composition containing the co-crystal of any one of (1) to (6).

(12) The agrochemical composition according to (11), wherein the agrochemical composition is an insecticide.

(13) A seed treatment agent containing the co-crystal of any one of (1) to (6).

(14) The seed treatment agent according to (13), wherein the seed treatment agent is an aquatic suspended concentrate composition.

(15) A method for treating a seed, including: coating a seed with the agrochemical composition containing the co-crystal of any one of (1) to (6).

Effects of the Invention

The water solubility of the neonicotinoid-based insecticidal-active ingredient in the co-crystal according to the present invention is lower than the water solubility of the neonicotinoid-based insecticidal-active ingredient itself. An agrochemical composition such as an insecticidal composition containing the co-crystal according to the present invention realizes elution of a diamide-based insecticidal-active ingredient and a neonicotinoid-based insecticidal-active ingredient into water at an adequate rate, and thereby excellent insecticidal effects are maintained over a long period of time and there is no concern of phytotoxicity on useful plants or the like.

EMBODIMENTS FOR CARRYING OUT THE INVENTION

A co-crystal according to the present invention consists of a diamide-based insecticidal-active ingredient and a neonicotinoid-based insecticidal-active ingredient.

There is no particular limitation on the neonicotinoid-based insecticidal-active ingredient, provided that the neonicotinoid-based insecticidal-active ingredient belongs to a compound group which exhibits an insecticidal effect as a nicotinic acetylcholine receptor agonist or antagonist. Specific examples thereof include a compound of Formula (1).

[Chemical formula 3]

(1)

In the formula, $R^1$ represents $CHR^{11}R^{12}$, $NR^{11}R^{12}$, or $SR^{12}$, and preferably represents $CHR^{11}R^{12}$.

$R^{11}$ and $R^{12}$ each independently represents a hydrogen atom, or a C1-2 alkyl group. Specific examples of the C1-2 alkyl group include a methyl group, and an ethyl group.

$R^2$ represents a halogen atom, a cyano group, a nitro group, or an unsubstituted or substituted C1-6 acyl group. Specific examples of the halogen atom include a fluorine atom, a chlorine atom, a bromine atom, and an iodine atom. Examples of the C1-6 acyl group include a formyl group, an acetyl group, and a propionyl group. Among these, $R^2$ preferably represents a cyano group.

$R^3$ represents a hydrogen atom, a C1-6 alkyl group, a C1-6 haloalkyl group, or a C3-6 cycloalkyl group. Specific examples of the C1-6 alkyl group include a methyl group, an ethyl group, a n-propyl group, an i-propyl group, a n-butyl group, a s-butyl group, an i-butyl group, a t-butyl group, a n-pentyl group, and a n-hexyl group. Examples of the C1-6 haloalkyl group include a monofluoromethyl group, a difluoromethyl group, a trifluoromethyl group, a trichloromethyl group, a 2,2,2-trifluoroethyl group, a perfluoroethyl group, a 2,2,2-trichloroethyl group, a 1,1,1,3,3,3-hexafluoro-2-propyl group, a perfluoron-propyl group, and a 4,4,4-trifluoro-n-butyl group. Examples of the C3-6 cycloalkyl group include a cyclopropyl group, a cyclobutyl group, a cyclopentyl group, and a cyclohexyl group. Among these, $R^3$ preferably represents a C1-6 alkyl group.

$R^4$ represents a hydrogen atom or a methyl group, and preferably represents a hydrogen atom.

Het represents an unsubstituted or substituted 5- to 6-membered heterocyclic group. The 5- to 6-membered heterocyclic group preferably has at least one hetero atom selected from the group consisting of an oxygen atom, a sulfur atom, and a nitrogen atom, and specific examples thereof include a pyrrolyl group, a furyl group, a thienyl group, an imidazolyl group, a pyrazolyl group, an oxazolyl group, an isooxazolyl group, a thiazolyl group, an isothiazolyl group, a triazolyl group, an oxadiazolyl group, a thiadiazolyl group, a tetrazolyl group; a pyridyl group, a pyrazinyl group, a pyrimidinyl group, a pyridazinyl group, and a triazinyl group. These heterocyclic groups may have a substituent mentioned below. Among these, an unsubstituted or substituted pyridyl group is preferable, and a pyridyl group having a halogen atom as a substituent is more preferable.

A represents N or $CR^{13}$, in which $R^{13}$ represents a hydrogen atom or a C1-2 alkyl group. Specific examples of the C1-2 alkyl group include a methyl group and an ethyl group. Among these, A preferably represents N.

Any one of $R^2$ and $R^{13}$ and $R^1$, and, $R^{12}$ and $R^3$, may each independently form a 5- to 6-membered heterocyclic group, and examples of such a 5- to 6-membered heterocyclic group include pyrrole, thiophene, imidazole, pyrazole, oxazole, isoxazole, thiazole, isothiazole, triazole, oxadiazole, thiadiazole, tetrazole, pyridine, pyrazine, pyrimidine, pyridazine, and triazine. These heterocyclic group may have a substituent mentioned below.

Among the neonicotinoid-based insecticidal-active ingredients, imidacloprid, acetamiprid, thiamethoxam, thiacloprid, clothianidin, dinotefuran, nitenpyram, nithiazine, flonicamid, sulfoxaflor, flupyradifurone, paichongding, imidaclothiz, N-[3-[(6-chloro-3-pyridinyl)methyl]-2(3H)-thiazolylidene]-2,2,2-trifluoroacetamide, and N-[1-[(6-chloro-3-pyridinyl)methyl]-2(1H)-pyridinelidene]-2,2,2-trifluoroacetamide are preferable, imidacloprid, acetamiprid, thiamethoxam, clothianidin, thiacloprid, nitenpyram, N-[3-[(6-chloro-3-pyridinyl)methyl]-2(3H)-thiazolylidene]-2,2,2-trifluoroacetamide, and N-[1-[(6-chloro-3-pyridinyl)methyl]-2(1H)-pyridinelidene]-2,2,2-trifluoroacetamide, the water solubility of which are relatively high, are more preferable, and acetamiprid is even more preferable.

The diamide-based insecticidal-active ingredient belongs to a compound group that has a basic structure in which an aminocarbonyl group or a carbonylamino is bonded to a benzene ring, and an aryl group such as a phenyl group or a pyrazole group is bound to at least one position thereof, and is not particularly limited, provided that the diamide-based insecticidal-active ingredient exhibits activity as a ryanodine receptor agonist. Specific examples thereof include a compound of Formula (2).

[Chemical formula 4]

(2)

In Formula (2), Q represents $CR^{14}$ or a nitrogen atom, in which $R^{14}$ represents a hydrogen atom, an unsubstituted or substituted C1-6 alkyl group, an unsubstituted or substituted C2-6 alkenyl group, or an unsubstituted or substituted C2-6 alkynyl group. Specific examples of the C1-6 alkyl group include a methyl group, an ethyl group, a n-propyl group, an i-propyl group, a n-butyl group, a s-butyl group, an i-butyl group, a t-butyl group, a n-pentyl group, and a n-hexyl group. Examples of the C2-6 alkenyl group include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group. Examples of the C2-6 alkynyl group include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group. Among these, Q preferably represents a nitrogen atom.

$R^5$ and $R^8$ each independently represents a halogen atom, a cyano group, a nitro group, an unsubstituted or substituted C1-6 alkyl group, an unsubstituted or substituted C2-6 alkenyl group, or an unsubstituted or substituted C2-6 alkynyl group. Specific examples of the halogen atom include a fluorine atom, a chlorine atom, a bromine atom, and an iodine atom. Examples of the C1-6 alkyl group, the C2-6 alkenyl group, and the C2-6 alkynyl group include the same groups mentioned for $R^{14}$. Among these, it is preferable that $R^5$ and $R^8$ each independently represents a halogen atom, a cyano group, or an unsubstituted or substituted C1-6 alkyl group.

n1 represents 0 or an integer of 1 to 3, and preferably represents 1.

n2 represents 0 or an integer of 1 to 4, and preferably represents 1 or 2.

$R^6$ represents a halogen atom, a cyano group, a nitro group, or an unsubstituted or substituted C1-6 acyl group. Specific examples of the C1-6 acyl group include a formyl group, an acetyl group, and a propionyl group. Among these, $R^6$ preferably represents a halogen atom.

$R^7$ represents a hydrogen atom, an unsubstituted or substituted C1-6 alkylthio group, or an unsubstituted or substituted C1-6 alkylsulfinyl group. Specific examples of the C1-6 alkylthio group include a methylthio group, an ethylthio group, a n-propylthio group, an i-propylthio group, a n-butylthio group, an i-butylthio group, a s-butylthio group, and a t-butylthio group. Examples of the C1-6 alkylsulfinyl group include a methylsulfinyl group, an ethylsulfinyl group, and a t-butylsulfinyl group. Among these, $R^7$ preferably represents a hydrogen atom.

$R^9$ represents an unsubstituted or substituted C1-6 alkyl group, an unsubstituted or substituted C2-6 alkenyl group, or an unsubstituted or substituted C2-6 alkynyl group. Specific examples thereof include the same groups mentioned for $R^{14}$. Among these, $R^9$ preferably represents an unsubstituted or substituted C1-6 alkyl group.

Among the diamide-based insecticidal-active ingredients, cyantraniliprole, chlorantraniliprole, cyclaniliprole, flubendiamide, and SYP-9080 are preferable, cyantraniliprole, chlorantraniliprole, and cyclaniliprole are more preferable, and cyantraniliprole is even more preferable.

The term "substituted" in Formulae (1) and (2) means that any hydrogen atom of a group which becomes a mother nucleus is substituted with a group having the same structure as that of the mother nucleus or different from that of the mother nucleus. The number of substituents may be one or two or more. The two or more substituents may be the same as or different from each other.

The term "C1-6" or the like represents that the number of carbon atoms of the group which becomes the mother nucleus is one to six. The number of carbon atoms does not include the number of carbon atoms existing in substituents. For example, a butyl group having an ethoxy group as a substituent is classified as a substituted C4 alkyl group.

The "substituent" is not particularly limited as long as it is chemically acceptable and exhibits effects of the present invention.

Specific examples of a group which can be the "substituent" include: halogen atoms, such as a fluorine atom, a chlorine atom, a bromine atom, and an iodine atom; C1-6 alkyl groups, such as a methyl group, an ethyl group, a n-propyl group, an i-propyl group, a n-butyl group, a s-butyl group, an i-butyl group, a t-butyl group, a n-pentyl group, and a n-hexyl group; C3-6 cycloalkyl groups, such as a cyclopropyl group, a cyclobutyl group, a cyclopentyl group, and a cyclohexyl group; C2-6 alkenyl groups, such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group; C3-6 cyclo alkenyl groups, such as a 2-cyclopropenyl group, a 2-cyclopentenyl group, and a 3-cyclohexenyl group; C2-6 alkynyl groups, such as an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and 1,1-dimethyl-2-butynyl group;

C1-6 alkoxy groups such as a methoxy group, an ethoxy group, a n-propoxy group, an i-propoxy group, a n-butoxy group, a s-butoxy group, an i-butoxy group, and a t-butoxy group; C2-6 alkenyloxy groups such as a vinyloxy group, an allyloxy group, a propenyloxy group, and a butenyloxy group; C2-6 alkynyloxy groups such as an ethynyloxy group, and a propargyloxy group; C3-6 cycloalkoxy groups such as a cyclopropyloxy group, a cyclobutyloxy group, a cyclopentyloxy group, and a cyclohexyloxy group; C6-10 aryl groups such as a phenyl group and a naphthyl group; C6-10 aryloxy groups such as a phenoxy group, a naphthoxy group, an azulenyloxy group, an indenyloxy group, an indanyloxy group, and a tetralinyloxy group; C7-14 aralkyl groups such as a benzyl group and a phenethyl group; C7-14 aralkyloxy groups such as a benzyloxy group and a phenethyloxy group; C1-11 acyl groups such as a formyl group, an acetyl group, a propionyl group, a benzoyl group, and a cyclohexylcarbonyl group; C1-7 acyloxy groups such as a formyloxy group, an acetyloxy group, a propionyloxy group, a benzoyloxy group, and a cyclohexyl carbonyloxy group; C1-6 alkoxycarbonyl groups such as a methoxycarbonyl group, an ethoxycarbonyl group, a n-propoxycarbonyl group, an i-propoxycarbonyl group, an n-butoxycarbonyl group, and a t-butoxycarbonyl group; a carboxyl group a hydroxyl group; C1-6 haloalkyl groups such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, a 2,2,2-trifluoro-1-trifluoromethyl-ethyl group, a perfluorohexyl group, a perchlorohexyl group, and a 2,4,6-trichlorohexyl group; C2-6 haloalkenyl groups such as a 2-chloro-1-propenyl group and a 2-fluoro-1-butenyl group; C2-6 haloalkynyl groups such as a 4,4-dichloro-1-butynyl group, a 4-fluoro-1-pentynyl group, and a 5-bromo-2-pentynyl group; C1-6 haloalkoxy groups such as a chloromethoxy group, a dichloromethoxy group, a trichloromethoxy group, a trifluoromethoxy group, a 1-fluoroethoxy group, a 1,1-difluoroethoxy group, a 2,2,2-trifluoroethoxy group, a pentafluoroethoxy group, a 2-chloro-n-propoxy group, and a 2,3-dichlorobutoxy group; C2-6 haloalkenyloxy groups such as a 2-chloropropenyloxy group, and a 3-bromobutenyloxy group; C6-10 haloaryl groups such as a 4-chlorophenyl group, a 4-fluorophenyl group, and a 2,4-dichlorophenyl group; C6-10 haloaryloxy groups such as a 4-fluorophenoxy group and a 4-chloro-1-naphthoxy group; C1-7 haloacyl groups such as a monofluoroacetyl group, a monochloroacetyl group, a monobromoacetyl group, a difluoroacetyl group, a dichloroacetyl group, a dibromoacetyl group, a trifluoroacetyl group, a trichloroacetyl group, a tribromoacetyl group, a 3,3,3-trifluoropropionyl group, a 3,3,3-trichloropropionyl group, a 2,2,3,3,3-pentafluoropropionyl group, and a 4-chlorobenzoyl group;

a cyano group; an isocyano group; a nitro group; an isocyanato group; a cyanato group; an azido group; an amino group; C1-6 (di)alkylamino groups such as a methylamino group, a dimethylamino group, and a diethylamino group; C6-10 arylamino groups such as an anilino group, and a naphthylamino group; C7-11 aralkylamino groups such as a benzylamino group and a phenylethyl amino group; C1-7 acylamino groups such as a formylamino group, an acetylamino group, a propanoylamino group, a butyrylamino group, an i-propylcarbonylamino group, and a benzoylamino group; C1-6 alkoxycarbonylamino groups such as a methoxycarbonylamino group, an ethoxycarbonylamino group, an n-propoxycarbonylamino group, and an i-propoxycarbonylamino group;

a mercapto group; an isothiocyanato group; a thiocyanato group; C1-6 alkylthio groups such as a methylthio group, an ethylthio group, a n-propylthio group, an i-propylthio group, a n-butylthio group, an i-butylthio group, a s-butylthio group, and a t-butylthio group; C2-6 alkenylthio groups such as a vinylthio group and an allylthio group; C2-6 alkynylthio groups such as an ethynylthio group and a propargylthio group; C6-10 arylthio groups such as a phenylthio group and a naphthylthio group; heteroarylthio groups such as a thiazolylthio group and a pyridylthio group; C7-14 aralkylthio groups such a benzylthio group and a phenethylthio group; acylthio group (preferably C1-6 acylthio group) such as an acetylthio group, and a benzoylthio group; (C1-6 alkylthio) carbonyl groups such as a (methylthio)carbonyl group, an (ethylthio)carbonyl group, a (n-propylthio)carbonyl group, an (i-propylthio)carbonyl group, a (n-butylthio)carbonyl group, an (i-butylthio)carbonyl group, a (s-butylthio)carbonyl group, and a (t-butylthio)carbonyl group;

C1-6 alkylsulfinyl groups such as a methylsulfinyl group, an ethylsulfinyl group, and a t-butyl sulfinyl group; C2-6 alkenyl sulfinyl groups such as an allyl sulfinyl group; C2-6 alkynylsulfinyl groups such as a propargylsulfinyl group; C6-10 arylsulfinyl groups such as a phenylsulfinyl group; heteroarylsulfinyl groups such as a thiazoylsulfinyl group and a pyridylsulfinyl group; C7-11 aralkylsulfinyl groups such as a benzyl sulfinyl group and a phenethylsulfinyl group; C1-6 alkylsulfonyl groups such as a methyl sulfonyl group, an ethyl sulfonyl group, and a t-butyl sulfonyl group; C2-6 alkenylsulfonyl groups such as an allyl sulfonyl group; C2-6 alkynylsulfonyl groups such as a propargylsulfonyl group; C6-10 arylsulfonyl groups such as a phenylsulfonyl group; heteroarylsulfonyl groups such as a thiazolylsulfonyl group and a pyridylsulfonyl group; C7-14 aralkylsulfonyl groups such as a benzylsulfonyl group and a phenethylsulfonyl group; haloalkylsulfonyl groups (preferably C1-6 haloalkylsulfonyl groups) such as a trifluoromethylsulfonyl group; a sulfo group; alkoxysulfonyl groups (preferably C1-6 alkoxysulfonyl groups) such as a methoxysulfonyl group, and an ethoxysulfonyl group; a sulfamoyl group; sulfamoyl groups (preferably mono C1-6 alkylsulfamoyl group or di C1-6 alkylsulfamoyl group) such as a N-methylsulfamoyl group, a N-ethylsulfamoyl group, a N,N-dimethylsulfamoyl group, and a N,N-diethylsulfamoyl group; monoarylsulfamoyl group (preferably mono C6-10 arylsulfamoyl group) such as a phenylsulfamoyl group, and a 4-methylphenylsulfamoyl group;

5-membered heteroaryl groups such as a pyrrolyl group, a furyl group, a thienyl group, an imidazolyl group, a pyrazolyl group, an oxazolyl group, an isoxazolyl group, a thiazolyl group, an isothiazolyl group, an triazolyl group, an oxadiazolyl group, a thiadiazolyl group, and a tetrazolyl group; 6-membered heteroaryl groups such as a pyridyl group, a pyrazinyl group, a pyrimidinyl group, a pyridazinyl group, and a triazinyl group; saturated heterocyclic groups such as an aziridinyl group, an epoxy group, a pyrrolidinyl group, a tetrahydrofuranyl group, a piperidyl group, a piperazinyl group, and a morpholinyl group; —Si($R^{20}$)($R^{21}$)($R^{22}$) (wherein $R^{20}$, $R^{21}$, and $R^{22}$, each independently represents a C1-6 alkyl group or a phenyl group, and examples of the C1-6 alkyl group include the same groups mentioned above), such as a trimethylsilyl group, a triethylsilyl group, a t-butyldimethylsilyl group, a tricyclopropyl group, and a triphenylsilyl group.

In addition, these "substituents" may further have another "substituent" therein, and specific examples thereof include: "C1-6 alkyl groups" substituted with "unsubstituted or substituted C3-6 cycloalkyl groups" such as a cyclopropylmethyl group, a 2-cyclopropylethyl group, a cyclopentylmethyl group, and a 2-cyclohexylethyl group; "C1-6 alkyl groups" substituted with "unsubstituted or substituted C3-6 cycloalkenyl groups", such as a cyclopentenylmethyl group, a 3-cyclopentatenylmethyl group, a 3-cyclohexenylmethyl group, a 2-(3-cyclohexenyl)ethyl group; "C1-6 alkyl groups" substituted with "unsubstituted or substituted heterocyclic groups", such as a 2-pyridylmethyl group, a 3-pyridylmethyl group, a 4-pyridylmethyl group, a 2-(2-pyridyl)ethyl group, a 2-(3-pyridyl)ethyl group, a 2-(4-pyridyl)ethyl group, a 3-(2-pyridyl)propyl group, a 3-(3-pyridyl)propyl group, a 3-(4-pyridyl)propyl group, a 2-pyrazinylmethyl group, a 3-pyrazinylmethyl group, a 2-(2-pyrazinyl)ethyl group, a 2-(3-pyrazinyl)ethyl group, a 3-(2-pyrazinyl)propyl group, a 3-(3-pyrazinyl)propyl group, a 2-pyrimidylmethyl group, a 4-pyrimidylmethyl group, a 2-(2-pyrimidyl)ethyl group, a 2-(4-pyrimidyl)ethyl group, a 3-(2-pyrimidyl)propyl group, a 3-(4-pyrimidyl)propyl group, a 2-furylmethyl group, a 3-furylmethyl group, a 2-(2-furyl)ethyl group, a 2-(3-furyl)ethyl group, a 3-(2-furyl)propyl group, and a 3-(3-furyl)propyl group; "C1-6 alkyl groups" substituted with "a hydroxyl group", such as a hydroxymethyl group, a hydroxyethyl group, and a hydroxypropyl group; "hydroxyl C1-20 alkyl groups" substituted with "unsubstituted or substituted C1-6 alkyl groups", such as a methoxymethyl group, an ethoxymethyl group, a methoxyethyl group, an ethoxyethyl group, a methoxy n-propyl group, an ethoxymethyl group, an ethoxyethyl group, a n-propoxymethyl group, an i-propoxyethyl group, a s-butoxymethyl group, a t-butoxyethyl group, and a 2,2-dimethoxyethyl group; "hydroxy C1-6 alkyl groups" substituted with "unsubstituted or substituted C1-20 acyl groups", such as a formyloxymethyl group, an acetoxymethyl group, a 2-acetoxyethyl group, a propionyloxymethyl group, and a propionyloxyethyl group; "C3-6 cycloalkyl groups" substituted with "unsubstituted or substituted C1-6 alkyl groups", such as a 2,3,3-trimethylcyclobutyl group, a 4,4,6,6-tetramethylcyclohexyl group, and a 1,3-dibutylcyclohexyl group; "C4-6 cycloalkenyl groups" substituted with "unsubstituted or substituted C1-6 alkyl groups" such as a 2-methyl-3-cyclohexenyl group, and a 3,4-dimethyl-3-cyclohexenyl group; "C2-6 alkenyl groups" substituted with "halogen atoms", such as a 3-chloro-2-propenyl group, a 4-chloro-2-butenyl group, a 4,4-dichloro-3-butenyl group, a 4,4-difluoro-3-butenyl group, a 3,3-dichloro-2-propenyl group, a 2,3-dichloro-2-propenyl group, a 3,3-difluoro-2-propenyl group, and a 2,4,6-trichloro-2-hexenyl group; "C2-6 alkynyl groups" substituted with "halogen atoms", such as a 3-chloro-1-propynyl group, a 3-chloro-1-butynyl group, a 3-bromo-1-butynyl group, a 3-bromo-2-propynyl group, a 3-iodo-2-propynyl group, a 3-bromo-1-hexynyl group, a 4,4,6,6-tetrafluoro-1-dodecynyl group, a 5,5-dichloro-2-methyl-3-pentynyl group, and a 4-chloro-1,1-dimethyl-2-butynyl group; "alkoxy groups" substituted with "unsubstituted or substituted C3-6 cycloalkyl groups" or "unsubstituted or substituted C6-10 aryl groups", such as a cyclopropylmethyloxy group, a 2-cyclopentylethyloxy group, a benzyloxy group; cycloalkoxy groups substituted with "unsubstituted or substituted C1-6 alkyl groups", such as a 2-methylcyclopropyloxy group, a 2-ethylcyclopropyloxy group, a 2,3,3-trimethylcyclobutyloxy group, a 2-methylcyclopentyloxy group, a 2-ethylcyclohexyloxy group, a 4,4,6,6-tetramethylcyclohexyloxy group, and a 1,3-dibutylcyclohexyloxy group; "C1-6 acyl groups" substituted with "unsubstituted or substituted C2-6 alkenyl groups", "unsubstituted or substituted C2-6 alkynyl groups", "unsubstituted or substituted C6-10 aryl groups" or "unsubstituted or substituted heterocyclic groups", such as a 3-allyl-phenylcarbonyl group, a 3-ethynyl-phenylcarbonyl group, a benzylcarbonyl group, a phenethylcarbonyl group, or a 2-pyridylmethylcarbonyl group; "alkoxycarbonyl groups" substituted with "unsubstituted or substituted C3-6 cycloalkyl groups" or "unsubstituted or substituted C6-10 aryl groups", such as a cyclopropylmethyloxycarbonyl group, a 2-cyclopentylethyloxycarbonyl group, and a benzyloxycarbonyl group; "unsubstituted or substituted 1-(hydroximino) C1-6 alkyl groups", such as a hydroximinomethyl group, a 1-(hydroximino)ethyl group, a 1-(hydroximino)propyl group, and a 1-(hydroximino)butyl group; "unsubstituted or substituted 1-(hydroximino)C1-6 alkyl groups" in which a hydrogen atom on a hydroxyl group is substituted with an "unsubstituted or substituted C1-6 alkyl group", such as a methoximinomethyl group, an ethoximinomethyl group, and a 1-(ethoximino)ethyl group; "groups" having an amino group on which two hydrogen atoms are substituted with the same carbon atom of an "unsubstituted or substituted C1-6 alkyl group", such as a methylideneamino group, and an ethylideneamino group; diarylamino group (preferably di C6-10 arylamino group) such as a di 1-naphthylamino group; "carbamoyl groups" substituted with "unsubstituted or substituted C1-6 alkyl groups", such as a methylcarbamoyl group, an ethylcarbamoyl group, a dimethylcarbamoyl group, and a diethylcarbamoyl group; monoarylcarbamoyl groups (preferably mono C6-10 arylcarbamoyl groups) such as a phenylcarbamoyl group, and a 4-methylphenylcarbamoyl group; acylcarbamoyl groups (preferably C1-6 acylcarbamoyl groups)

such as an acetylcarbamoyl group, and a benzoylcarbamoyl group; "imino groups" substituted with "unsubstituted or substituted C6-10 alkyl groups", such as a methylimino group, and a benzylimino group; and "imino groups" substituted with "unsubstituted or substituted hydroxyl groups", such as a hydroximino group and an ethoximino group.

It is considered that the co-crystal according to the present invention is formed by stabilizing a diamide-based insecticidal-active ingredient and a neonicotinoid-based insecticidal-active ingredient through molecular interaction, such as hydrogen bonding, π-orbital stacking, or van der Waals force.

In the co-crystal according to the present invention, the molar ratio of the diamide-based insecticidal-active ingredient to the neonicotinoid-based insecticidal-active ingredient (the diamide-based insecticidal-active ingredient/the neonicotinoid-based insecticidal-active ingredient) is preferably within a range of 0.3 to 3.0, more preferably 0.5 to 2.0, still more preferably 0.8 to 1.25, and particularly preferably 0.9 to 1.1.

The formation of the co-crystal according to the present invention can be confirmed through thermal analysis (TG/DTA), differential scanning calorimetry (DSC), infrared absorption spectrum (IR), X-ray diffraction pattern, $^{13}$C-CP/MAS-solid NMR spectrum, or the like. In addition, the components of the co-crystal can be confirmed through thermal analysis, differential scanning calorimetry (DSC), $^{1}$H-NMR spectrum, $^{13}$C-NMR spectrum, $^{29}$Si-NMR spectrum, gel filtration chromatography (GPC), high performance liquid chromatography (HPLC), elemental analysis, or the like.

Examples of the method for producing the co-crystal according to the present invention include:
(i) a method including: mixing a diamide-based insecticidal-active ingredient and a neonicotinoid-based insecticidal-active ingredient, and an auxiliary ingredient as necessary; and subjecting the mixture to a mechanochemical solid phase reaction;
(ii) a method including: suspending a diamide-based insecticidal-active ingredient and a neonicotinoid-based insecticidal-active ingredient, and an auxiliary ingredient as necessary, in a solvent to obtain a suspension; and heating and stirring the suspension;
(iii) a method including: dissolving a diamide-based insecticidal-active ingredient and a neonicotinoid-based insecticidal-active ingredient, and an auxiliary ingredient as necessary, in a solvent, and then, depositing a co-crystal; and
(iv) a method including: mixing a diamide-based insecticidal-active ingredient and a neonicotinoid-based insecticidal-active ingredient, and an auxiliary ingredient as necessary; and heating to melt the mixture.

Among these, the method (ii) or (iii) is preferable.

Examples of the auxiliary ingredient to be used as necessary in the method for producing the co-crystal according to the present invention include a surfactant, an extending agent, an effect-reinforcing assistant, an antioxidant, an ultraviolet absorber, and a stabilizing agent.

The mechanochemical solid phase reaction in the method (i) is preferably performed by dry pulverization.

Although the solvent available in the method (ii) is not particularly limited, it is preferable that the solvent be a liquid medium in which at least one of the diamide-based insecticidal-active ingredient and the neonicotinoid-based insecticidal-active ingredient can be dissolved at a solubility of greater than or equal to 100 ppm. Examples of the solvent include: water; monohydric alcohols such as methanol, ethanol, propanol, isopropanol, and butanol; glycols such as ethylene glycol, diethylene glycol, propylene glycol, and glycerin; and ketone such as acetone, methylethyl ketone, and methylisobutyl ketone. The solvent may be used alone or in combination of two or more thereof. Among these, water is preferably used as the solvent.

After the diamide-based insecticidal-active ingredient and the neonicotinoid-based insecticidal-active ingredient are suspended in the solvent, the resultant may be stirred for a certain time or may be allowed to stand without being stirred. After the resultant is suspended, the resultant is heated and stirred for a certain time. The time for stirring or heating the resultant is not particularly limited, but a preferable range thereof is greater than or equal to 30 minutes but less than or equal to 1 day. The time depends on the intended use of the co-crystal, and any time may be set as long as at least a part of the diamide-based insecticidal-active ingredient and the neonicotinoid-based insecticidal-active ingredient, preferably 10% by mass to 100% by mass thereof, more preferably 50% by mass to 100% by mass thereof, and particularly preferably 90% by mass to 100% by mass thereof, form the co-crystal. The time can be determined by the above-described method for confirming the formation of the co-crystal, or measuring changes in solid particle size in the suspension over time. The heating temperature is preferably greater than or equal to 40° C. but lower than or equal to the boiling point of the solvent, and more preferably greater than or equal to 60° C. but lower than or equal to the boiling point of the solvent.

It is preferable that the above-mentioned step of heating and stirring the suspension be conducted in the presence of a surfactant. Although the following may be used as a surfactant, it is preferable that at least one selected from the group consisting of non-ionic surfactants such as polyoxyethylene glycol tristyrylphenyl ether, lignin sulfonate, and dialkylsulfo succinate be used.

The solvent available in the method (iii) is not particularly limited, provided that the diamide-based insecticidal-active ingredient and the neonicotinoid-based insecticidal-active ingredient can be entirely dissolved therein. Specific examples of the solvent include acetone, acetonitrile, methanol, ethanol, ethyl acetate, dichloromethane, chloroform, tetrahydrofuran, n-hexane, cyclohexane, benzene, toluene, and xylene. The solvent may be used alone or in combination of two or more thereof. Among these, acetone is preferable.

The deposition of the co-crystal may be performed by mixing the resultant with a poor solvent, or cooling the resultant. Although the following procedure is strictly different from the recrystallization procedure, the co-crystal can be obtained by solely distilling away the solvent.

In the method (iv), any heating temperature may be set, provided that the heating temperature is a temperature or higher at which at least the mixture of the diamide-based insecticidal-active ingredient and the neonicotinoid-based insecticidal-active ingredient is melted, and a temperature at which neither the diamide-based insecticidal-active ingredient nor the neonicotinoid-based insecticidal-active ingredient is decomposed. The temperature is not necessarily no less than melting temperatures independently shown by each of the above-described ingredients, and the temperature may be lower than the melting temperatures depending on the property of the above-described mixture. The heating temperature is preferably higher than or equal to 85° C., more preferably higher than or equal to 90° C., and even more preferably higher than or equal to 100° C.

The thus produced co-crystal can be used to produce an agrochemical composition according to the present invention, such as an insecticidal composition, in a form of being produced as it is or through further purifying the co-crystal, depending on the intended use.

The agrochemical composition according to the present invention, particularly the insecticidal composition, contains the co-crystal as an active ingredient thereof.

The co-crystal, as an active ingredient, may be contained alone or in combination of two or more thereof. The agrochemical composition according to the present invention may contain other agrochemical-active ingredients in addition to the co-crystal, and may contain an auxiliary ingredient, depending on the intended use and the dosage form.

Examples of other agrochemical-active ingredients which may be contained in the agrochemical composition according to the present invention include insecticides, acaricides, nematicides, fungicides, herbicides, plant growth regulators, resistance-inducing agents, pest repellents, and anti-viral agents, and more specific examples thereof include the following compounds.

Insecticide:
(1) Organic (thio)phosphate bases: acephate, azamethiphos, azinphos-methyl, azinphos-ethyl, buromophos-ethyl, bromfenvinphos, BRP, chlorpyrifos, chlorpyrifos-methyl, chlorfenvinphos, cadusafos, carbophenothion, chloroethoxyfos, chlormephos, coumaphos, cyanofenphos, cyanophos, dichlorvos, dicrotophos, dimethoate, disulfoton, demeton-S-methyl, dimethylvinphos, demeton-S-methylsulfone, dialifos, diazinon, dichlofenthion, dioxabenzophos, disulfoton, ethion, ethoprophos, etrimfos, EPN, fenamiphos, fenitrothion, fenthion, fensulfothion, fonofos, formothion, phosmethylan, heptenophos, isazophos, iodofenphos, isofenphos, isoxathion, malathion, mevinphos, methamidophos, methidathion, monocrotophos, mecarbam, methacrifos, omethoate, oxydemeton-methyl, parathion, parathion-methyl, phenthoate, phosalone, phosmet, phosphamidon, phorate, phoxim, pirimiphos-methyl, pirimiphos-ethyl, profenofos, prothiofos, fosthiazate, phosphocarb, propaphos, propethamphos, prothoate, pyridaphenthion, pyraclofos, quinalphos, sulprophos, sulfotepp, tetrachlorvinphos, terbufos, triazophos, trichlorfon, tebupirimfos, temephos, thiometon, vamidothion, and imicyafos;

(2) Carbamate bases: alanycarb, aldicarb, bendiocarb, benfuracarb, carbaryl, carbofuran, carbosulfan, phenothiocarb, methiocarb, methomyl, oxamyl, pirimicarb, propoxur, thiodicarb, ethiofencarb, fenobucarb, MIPC, MPMC, MTMC, furathiocarb, XMC, aldoxicarb, allyxycarb, aminocarb, bufencarb, butacarb, butocarboxim, butoxycarboxim, cloethocarb, dimetilan, formetanate, metam-sodium, metolcarb, promecarb, thiophanox, trimethacarb, and xylylcarb;

(3) Pyrethroid bases: allethrin, bifenthrin, cyfluthrin, beta-cyfluthrin, cyhalothrin, lambda-cyhalothrin, cyphenothrin, cypermethrin, alpha-cypermethrin, beta-cypermethrin, zeta-cypermethrin, deltamethrin, esfenvalerate, ethofenprox, fenpropathrin, fenvalerate, imiprothrin, permethrin, prallethrin, pyrethrin, pyrethrin I, pyrethrin II, resmethrin, silafluofen, fluvalinate, tefluthrin, tetramethrin, tralomethrin, transfluthrin, profluthrin, dimefluthrin, acrinathrin, cycloprothrin, halfenprox, flucythrinate, bioallethrin, bioethanomethrin, biopermethrin, bioresmethrin, transpemethrin, empenthrin, fenfluthrin, fenpirithrin, flubrocythrinate, flufenprox, flumethrin, metofluthrin, phenothrin, protrifenbute, pyresmethrin, terallethrin, meperflutherin, and tetramethylfluthrin;

(4) Growth-regulating substances:
  (a) Chitin synthesis inhibitors: chlorfluazuron, diflubenzuron, flucycloxuron, flufenoxuron, hexaflumuron, lufenuron, novaluron, teflubenzuron, triflumuron, bistrifluron, noviflumuron, buprofezin, fluazuron, and penfluron;
  (b) Ecdysone agonists: halofenozide, methoxyfenozide, tebufenozide, chromafenozide, and azadirachtin;
  (c) Juvenile hormone analogs: pyriproxyfen, methoprene, epofenonane, hydroplane, kinoprene, triprene, diofenolan, and fenoxycarb; and
  (d) Lipid biosynthesis inhibitors: spirodiclofen, spiromesifen, and spirotetramat;

(5) Nicotine receptor agonist/antagonist compounds: nicotine, bensultap, cartap, thiocyclam, thiosultap, and nereistoxin;

(6) GABA antagonist compounds: acetoprole, ethiprole, fipronil, vaniliprole, pyrafluprole, and pyriprole;

(7) Macrocyclic lactone insecticides: abamectin, emamectin benzoate, milbemectin, lepimectin, spinosad, ivermectin, selamectin, doramectin, eprinomectin, moxidectin, milbemycin oxime, and spinetoram;

(8) METI I compounds: fenazaquin, pyridaben, tebufenpyrad, tolfenpyrad, flufenerim, fenpyroximate, and pyrimidifen;

(9) METI II and III compounds: acequinocyl, fluacrypyrim, hydramethylnon, and cyenopyrafen;

(10) Uncoupler compounds: chlorfenapyr, binapacryl, dinobuton, dinocap, and DNOC;

(11) Oxidative phosphorylation inhibitor compounds: cyhexatin, diafenthiuron, fenbutatin-oxide, propargite, azocyclotin, and tetradifon;

(12) Molting-disrupting compounds: cyromazine;

(13) Mixed function oxidase inhibitor compounds: piperonyl butoxide;

(14) Sodium channel blocker compounds: indoxacarb and metaflumizone;

(15) Microbial agrochemicals: a BT agent, an insect pathogenic virus agent, an insect pathogenic filamentous fungus agent, and a nematode pathogenic filamentous fungus agent; the genus and species *Bacillus*, silkworm fungus, blackworm fungus, the genus and species *Paecilomyces*, thuringiensin, and the genus and species *Verticillium*;

(16) Latrophilin receptor agonist: emodepside;

(17) Octopamine-related agonist: amitraz;

(20) Feeding inhibitors: pymetrozine, flonicamid, and chlordimeform;

(21) Mite growth inhibitors: clofentezine, etoxazole, and hexythiazox;

(22) Other compounds: benclothiaz, bifenazate, pyridalyl, sulfur, cyflumetofen, amidoflumet, 1,3-dichloropropene, DCIP, metaldehyde, pyrifluquinazon, benzoximate, bromopropylate, chinomethionate, chloropicrin, dicyclanil, fenoxacrim, fentrifanil, flubenzimine, gossyplure, japonilure, metoxadiazon, oil, potassium oleate, sulfluramid, tetrasul, triarathene; afidopyropen, pyflubumide, flometoquin, fluensulfone, tralopyril, diflovidazin, methylneodecanamide, and triazamate;

(23) Anthelmintics
  (a) Benzimidazole bases: fenbendazole, albendazole, triclabendazole, and oxybendazole;
  (b) Salicylanilide bases: closantel and oxyclozanide
  (c) Substituted phenol base: nitroxinil;
  (d) Pyrimidine base: pyrantel;
  (e) Imidazothiazole base: levamisole;
  (f) Tetrahydropyrimidine: praziquantel; and
  (g) Other anthelmintics: cyclodiene, ryania, clorsulon, metronidazole, and demiditraz.

Fungicides:

(1) Benzimidazole bases: benomyl, carbendazim, fuberidazole, thiabendazole, thiophanate-methyl, chlorofenazole, and debacarb;

(2) Dicarboximide bases: chlozolinate, iprodione, procymidone, and vinclozolin;

(3) DMI-fungicide bases: imazalil, oxpoconazole, pefurazoate, prochloraz, triflumizole, triforine, pyrifenox, fenarimol, nuarimol, azaconazole, bitertanol, bromuconazole, cyproconazole, difenoconazole, diniconazole, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole, etaconazole, and furconazole-cis; diclobutrazol, diniconazole-M, dodemorph acetate, fluconazole, imazalil-sulfate, naftifine, uniconazole P, viniconazole, and voriconazole;

(4) Phenyl amide bases: benalaxyl, benalaxyl-M, clozylacon, furalaxyl, metalaxyl, metalaxyl-M, oxadixyl, and ofurace;

(5) Amine bases: aldimorph, dodemorph, fenpropimorph, tridemorph, fenpropidin, piperalin, and spiroxamine;

(6) Phosphorothiorate bases: EDDP, iprobenfos, and pyrazophos;

(7) Dithiolane base: isoprothiolane;

(8) Carboxamide: benodanil, boscalid, carboxin, fenfuran, flutolanil, furametpyr, mepronil, oxycarboxin, penthiopyrad, thifluzamide, bixafen, isopyrazam, penflufen, fluxapyroxad, sedaxane, and fluopyram;

(9) Hydroxy-(2-amino)pyrimidine bases: bupirimate, dimethirimol, and ethirimol;

(10) AP fungicide (anilinopyrimidine) bases: cyprodinil, mepanipyrim, pyrimethanil, and andoprim;

(11) N-phenyl carbamate base: diethofencarb;

(12) QoI-fungicide (Qo inhibitor) bases: azoxystrobin, picoxystrobin, pyraclostrobin, kresoxim-methyl, trifluoxystrobin, dimoxystrobin, metominostrobin, orysastrobin, famoxadone, fluoxastrobin, fenamidone, and metominofen; ametoctradin, pyrametostrobin, pyraoxystrobin, pyribencarb; coumethoxystrobin, coumoxystrobin, enestroburin, phenoxystrobin, and triclopyricarb;

(13) PP fungicide (phenylpyrrole) bases: fenpiclonil and fludioxonil;

(14) Quinoline base: quinoxyfen;

(15) AH fungicide (aromatic hydrocarbon) bases: biphenyl, chloroneb, dicloran, quintozene, tecnazene, and chlorothalonil;

(16) MBI-R bases: fthalide, pyroquilon, and tricyclazole;

(17) MBI-D bases: carpropamid, diclocymet, and fenoxanil;

(18) SBI agent: fenhexamid;

(19) Phenyl urea: pencycuron;

(20) QiI-fungicides (Qi inhibitors): cyazofamid, amisulbrom, and frumecyclox;

(21) Benzamide bases: zoxamide and zarilamide;

(22) Enopyranuron bases: blasticidin and mildiomycin;

(23) Hexopyranosyl bases: kasugamycin and kasugamycin hydrochloride;

(24) Glucopyranosyl bases: streptomycin and validamycin;

(25) Cyanoacetamide: cymoxanil;

(26) Carbamates: iodocarb, propamocarb, prothiocarb, and polycarbamate;

(27) Uncoupling agents: binapacryl, dinocap, ferimzone, fluazinam, and meptyldinocap;

(28) Organic tin compounds: triphenyltin acetate, triphenyltin chloride, and triphenyltin hydroxide;

(29) Phosphate esters: phosphorous acid, tolclofos methyl, fosetyl, and adifenphos;

(30) Phthalamic acid base: techlofthalam;

(31) Benzotriazine base: triazoxide;

(32) Benzene sulfonamide base: flusulfamide;

(33) Pyridazinone: diclomezine;

(34) CAA fungicide (carboxylic acid amide) bases: dimethomorph, flumorph, benthiavalicarb-isopropyl, iprovalicarb, mandipropamid, and valifenalate;

(35) Tetracycline: oxytetracycline;

(36) Thiocarbamate base: methasulfocarb;

(37) Resistance-inducing agents: acibenzolar-S-methyl, probenazole, thiazinyl, and isotianil;

(38) Other compounds: etridiazole, polyoxin, polyoxorim, oxolinic acid, hydroxy isoxazole, octhilinone, silthiofam, diflumetrim, ethaboxam, cyflufenamid, proquinazid, metrafenone, fluopicolide, Bordeaux mixtures, copper naphthalate, copper oxide, oxycopper chloride, copper sulfate, mancopper, copper (II) bis(8-quinolinolato), copper (II) hydroxide, organocopper, sulfur, calcium polysulfide, ferbam, manzeb, manebu, metiram, propineb, thiuram, zineb, ziram, captan, captafol, folpet, dichlofluanid, tolylfluanid, dodine, guazatine, iminoctadine, iminoctadine acetate, iminoctadine alkylbenzenesulfonate, anilazine, dithianon, dazomet, chinomethionate, cyprofuram, and fluoroimide; isofetamido, tolprocarb, fenpyrazamine, pyriofenone, and tebufloquin; fluoro folpet, propamidine; benthiazole, bethoxazin, capsaicin, cufraneb, mancozeb, dichlorophene, diphenylamine, flumetover, fluoroimide, flutianil, fosetyl-aluminum, fosetyl-calcium, fosetyl-sodium, irumamycin, methyl isothiocyanate (MITC), natamycin, nitrothal-isopropyl, propamocarb-fosetylate, pyrimorph, pyrrolnitrin, tolnifanide, and trichlamide;

<Plant Growth Regulators>

Abscisic acid, indolebutyric acid, uniconazole, ethchlozate, ethephone, cloxyfonac, chlormequat, chlorella extract, calcium peroxide, cyanamide, dichlorprop, gibberellin, daminozide, decyl alcohol, trinexapac-ethyl, mepiquat chloride, paclobutrazol, paraffin wax, pyraflufen ethyl, flurprimidol, prohydrojasmon, prohexadione calcium salt, benzylaminopurine, pendimethalin, forchlorfenuron, maleic hydrazide potassium, 1-naphthylacetamide, 4-CPA, MCPB, choline, butralin, 1-methylcyclopropene, aviglycine hydrochloride, and cyprosulfamide.

The dosage form of the agrochemical composition according to the present invention is not particularly limited, and examples thereof include powder, wettable powder, water-dispersible granule, suspension, and tablet, and suspension concentrate is particularly preferable for a seed-coating agent.

Examples of the auxiliary ingredient available in the agrochemical composition according to the present invention include a surfactant, an extending agent, an effect-reinforcing assistant, an antioxidant, an ultraviolet absorber, and a stabilizing agent.

The surfactant available in the present invention may be selected depending on the dosage form and the intended use, and specific examples thereof include: nonionic surfactants such as alkyl phenyl ethers to which polyoxyethylene is added, alkyl ethers to which polyoxyethylene is added, higher fatty acid ester to which polyoxyethylene is added, sorbitan higher fatty acid ester to which polyoxyethylene is added, and polyoxyethylene glycol tristyryl phenyl ether; formaldehyde condensates such as sulfuric acid ester salts of alkyl phenyl ether to which polyoxyethylene is added, alkyl benzene sulfonates, sulfuric acid ester salts of higher alcohols, alkyl naphthalene sulfonates, polycarboxylates, lignin sulfonates, and alkyl naphthalene sulfonate; and isobutylene maleic anhydride copolymer.

The extending agent available in the present invention may be selected depending on the dosage form and the intended use, and examples thereof include: solvents, such as, water, glycerin, ethylene glycol, propylene glycol, dimethyl sulfoxide, dimethylacetamide, N-methylpyrrolidone, γ-butyrolactone, alcohols, aliphatic hydrocarbons, and aromatic hydrocarbons; thickeners, stabilizers, and binders, such as, polyvinyl pyrrolidone, polyvinyl alcohol, polyvinyl acetate, polyethylene glycol, carboxymethyl cellulose, hydroxypropyl cellulose, gum arabic, xanthan gum, gelatin, casein, pectin, and sodium alginate; solid carriers, such as, talc, clay, bentonite, kaolinite clay, montmorillonite, pyrophyllite, acid clay, diatomaceous earth, vermiculite, apatite, gypsum, mica, silica sand, calcium carbonate, and mineral powder such as pumice powder; white carbon (amorphous silica), and synthetic products such as titanium dioxide; crystalline cellulose, starch, plant-derived powders such as wood flour, cork, and coffee beans; polymer compounds such as polyvinyl chloride and petroleum resin; and water soluble components, such as, ammonium sulfate, ammonium nitrate, ammonium chloride, potassium phosphate, potassium chloride, urea, and sugar.

The method for producing the agrochemical composition according to the present invention is not particularly limited. Examples thereof include a method in which a co-crystal according to the present invention is formulated in a form of being produced as it is, or after being mixed with an auxiliary ingredient as necessary; a method in which a co-crystal according to the present invention is formulated after being isolated and then mixed with an auxiliary ingredient; and a method in which a diamide-based insecticidal-active ingredient and a neonicotinoid-based insecticidal-active ingredient that form a co-crystal are mixed with an auxiliary ingredient, the mixture is heated to form a co-crystal, an auxiliary ingredient is further added to the co-crystal, as necessary, and then the mixture is formulated.

Examples of the intended use of the agrochemical composition according to the present invention include agricultural and horticultural use, and home gardening use. It is preferable that the agrochemical use be insecticidal use, and specific examples of the insecticidal use include agricultural and horticultural use, home gardening use, and use in controlling sanitary insect pests, wood insect pests, termites, and ectoparasites or endoparasites on animals.

An application method of the agrochemical composition according to the present invention is not particularly limited, provided that the used dosage form can be applied to the application method. Specific examples thereof include foliage application; treatments onto propagating materials such as seeds, seed potatoes, and bulbs, by conducting spraying, dust coating, scattering, dipping, or the like; trunk injection; treatments onto soil or cultivation carriers by conducting surface scattering, mixing, irrigating, planting hole treatment, or the like; and application onto water surfaces of paddy fields.

The agrochemical composition according to the present invention is preferably used as a seed treatment agent. The seed treatment agent is preferably an aquatic suspended concentrate composition. The aquatic suspended concentrate composition may be preferably obtained in accordance with the method (ii) by suspending a diamide-based insecticidal-active ingredient and a neonicotinoid-based insecticidal-active ingredient, and an auxiliary ingredient, as necessary, in water to obtain a suspension, and then heating and stirring the suspension.

Examples of the method for treating seeds include a method in which seeds are coated with the agrochemical composition (seed treatment agent) according to the present invention. Specific examples thereof include a method in which the agrochemical composition according to the present invention is dissolved or dispersed in a sticker solution (a solution obtained by dissolving in water a water-soluble polymer such as PVA (polyvinyl alcohol) or CMC (carboxymethyl cellulose) to improve the adherability when seeds are treated, with a dye or another substance that serves as a mark of agent treatment), the obtained solution or dispersion is mixed with seeds of crops, and then drying the mixture to obtain seeds on which the agent uniformly adheres. In the case where the obtained seeds are sowed in the soil, the agent absorbed through the seed itself or the root sprouted from the seed is entirely spread over the plant, and the crops are protected from noxious insects.

EXAMPLES

Hereinafter, the present invention will be described in more detail with reference to the examples. However, the present invention is not limited thereto.

Example 1

4.7 parts by mass of acetamiprid (manufactured by Nippon Soda Co., Ltd), 10 parts by mass of cyantraniliprole (manufactured by Du Pont Kabushiki Kaisha) (molar ratio of cyantraniliprole to acetamiprid=approximately 1), and 7.91 parts by mass of acetone were put into an eggplant-shaped flask, and then stirred. The mixture was left for 1 day at room temperature. Then, acetone was distilled away by an evaporator at 50° C. to obtain a solid product.

Figure 1:
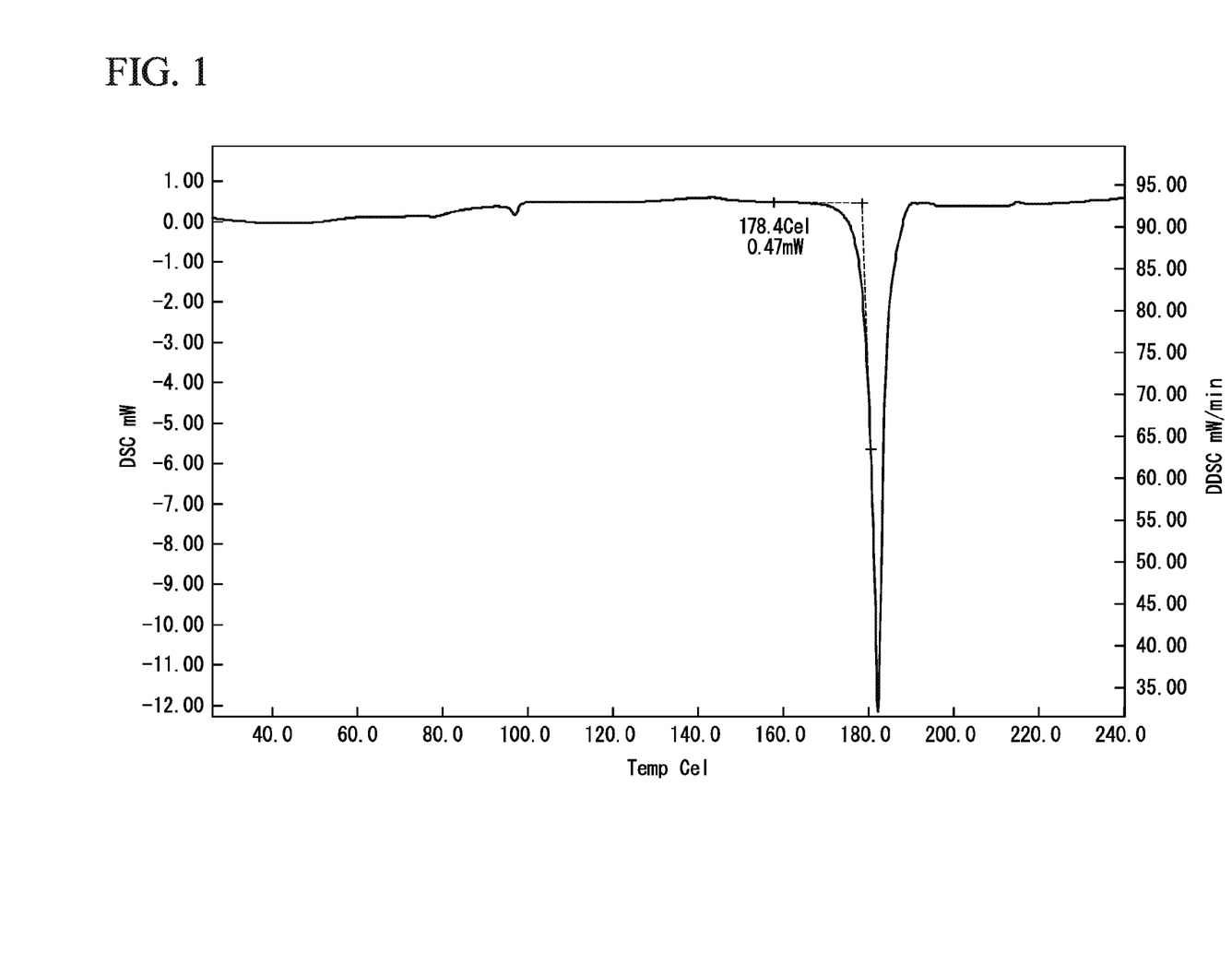
FIG. 1 is a view showing a result obtained by conducting differential scanning calorimetry (DSC measurement) of a co-crystal consisting of acetamiprid and cyantraniliprole.

The solid product was subjected to DSC measurement (measurement device: DSC 220 manufactured by Seiko Instruments Inc., the same measurement device was used in the following). The result is shown in FIG. 1. A melting point (approximately 178° C.) was found which was different from the melting points of acetamiprid and cyantraniliprole (FIG. 1). The melting point of acetamiprid is approximately 98° C. and the melting point of cyantraniliprole is 217° C. The longitudinal axis (left) of the DSC curve represents calories and the horizontal axis represents temperature.

Figure 3:
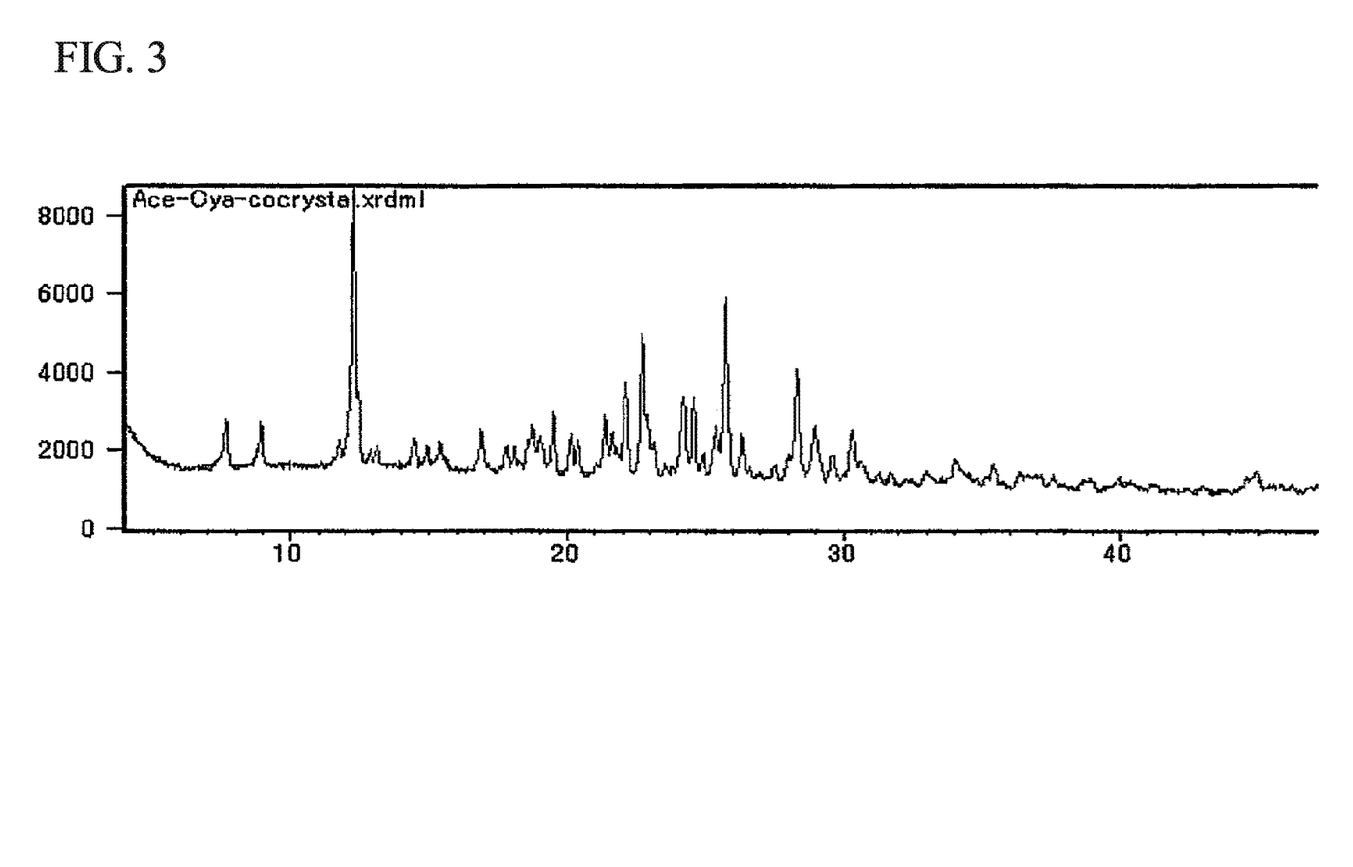
FIG. 3 is a view showing X-ray diffraction of the co-crystal consisting of acetamiprid and cyantraniliprole.
Figure 4:
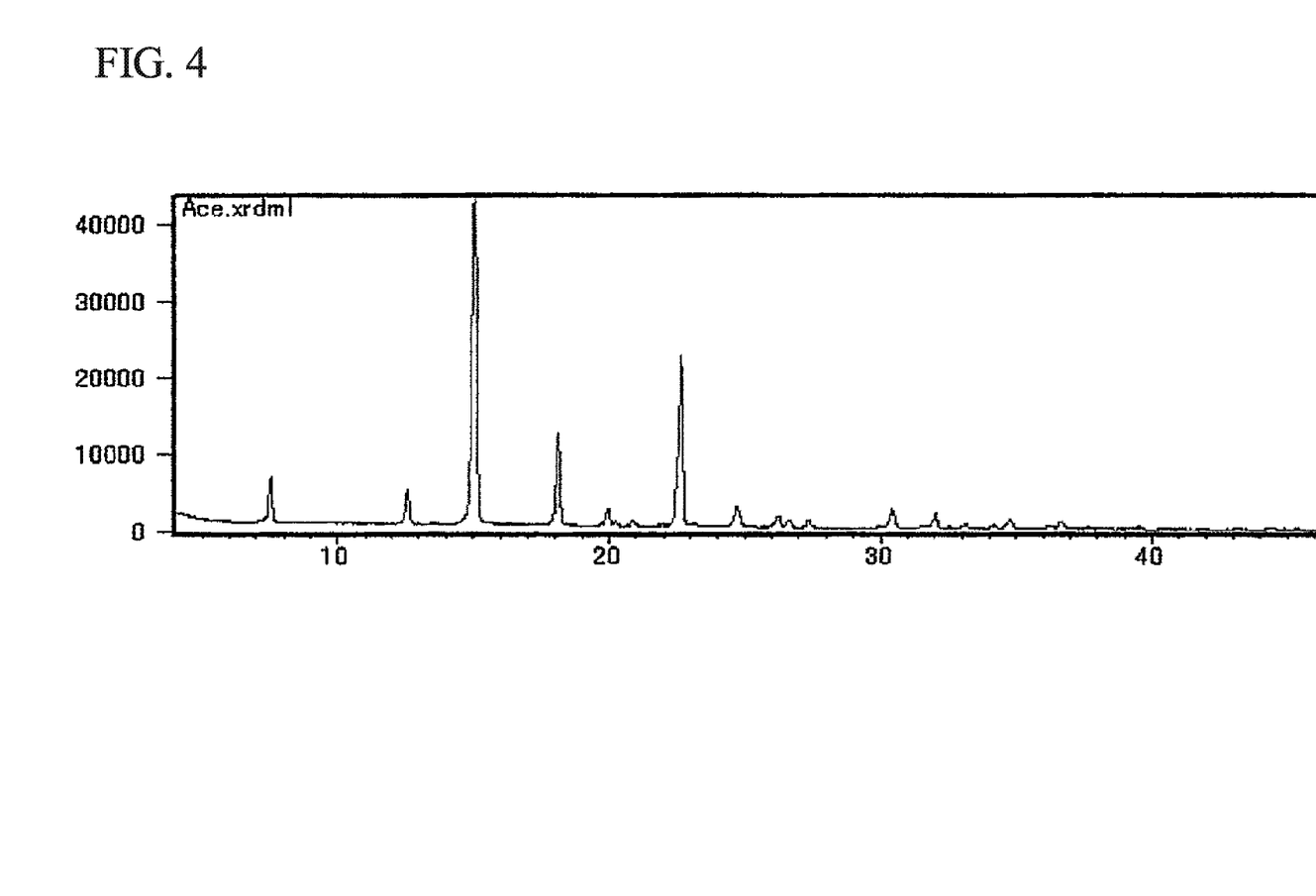
FIG. 4 is a view showing X-ray diffraction of acetamiprid.
Figure 5:
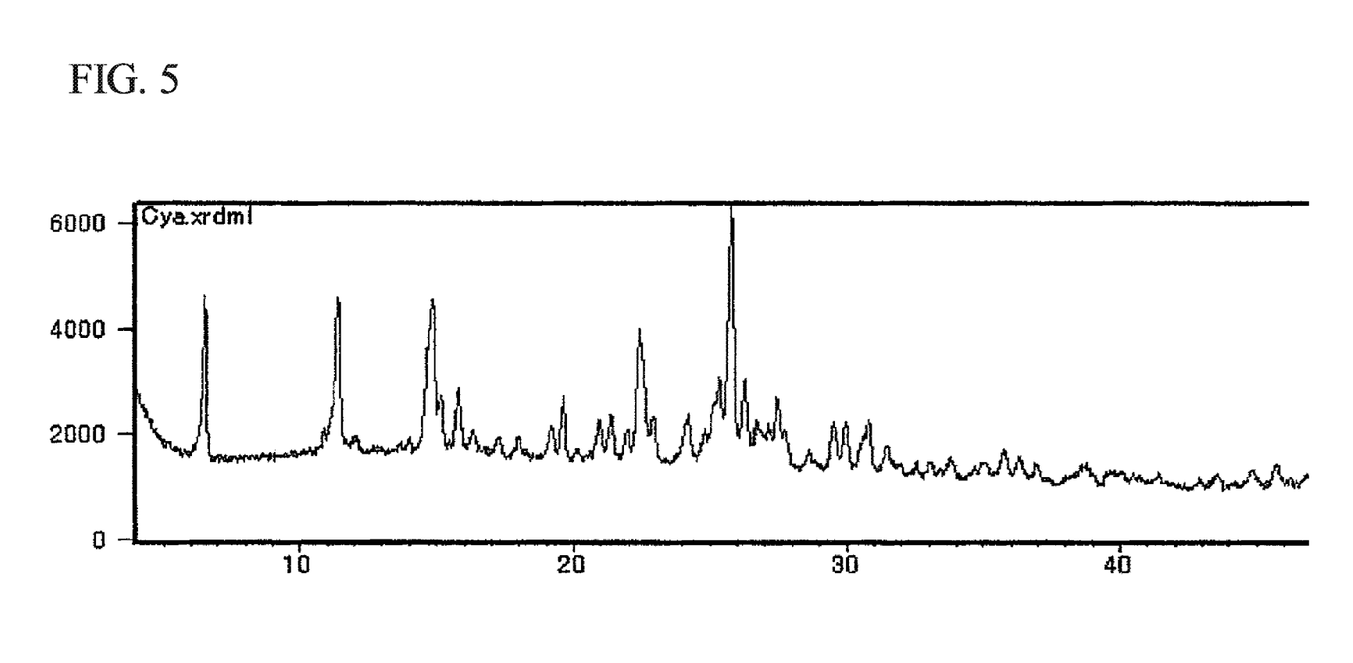
FIG. 5 is a view showing X-ray diffraction of cyantraniliprole.

Powder X-ray diffraction (XRD) of the solid product, acetamiprid, and cyantraniliprole was measured, and the results thereof are shown in FIGS. 3 to 5. The longitudinal axis represents intensity and the horizontal axis represents a diffraction angle. It can be seen that the solid product had a crystal structure different from those of acetamiprid and cyantraniliprole.

Accordingly, it is considered that the solid product generated in Example 1 was a co-crystal in which acetamiprid and cyantraniliprole were contained at a molar ratio of approximately 1:1.

Comparative Example 1

Figure 2:
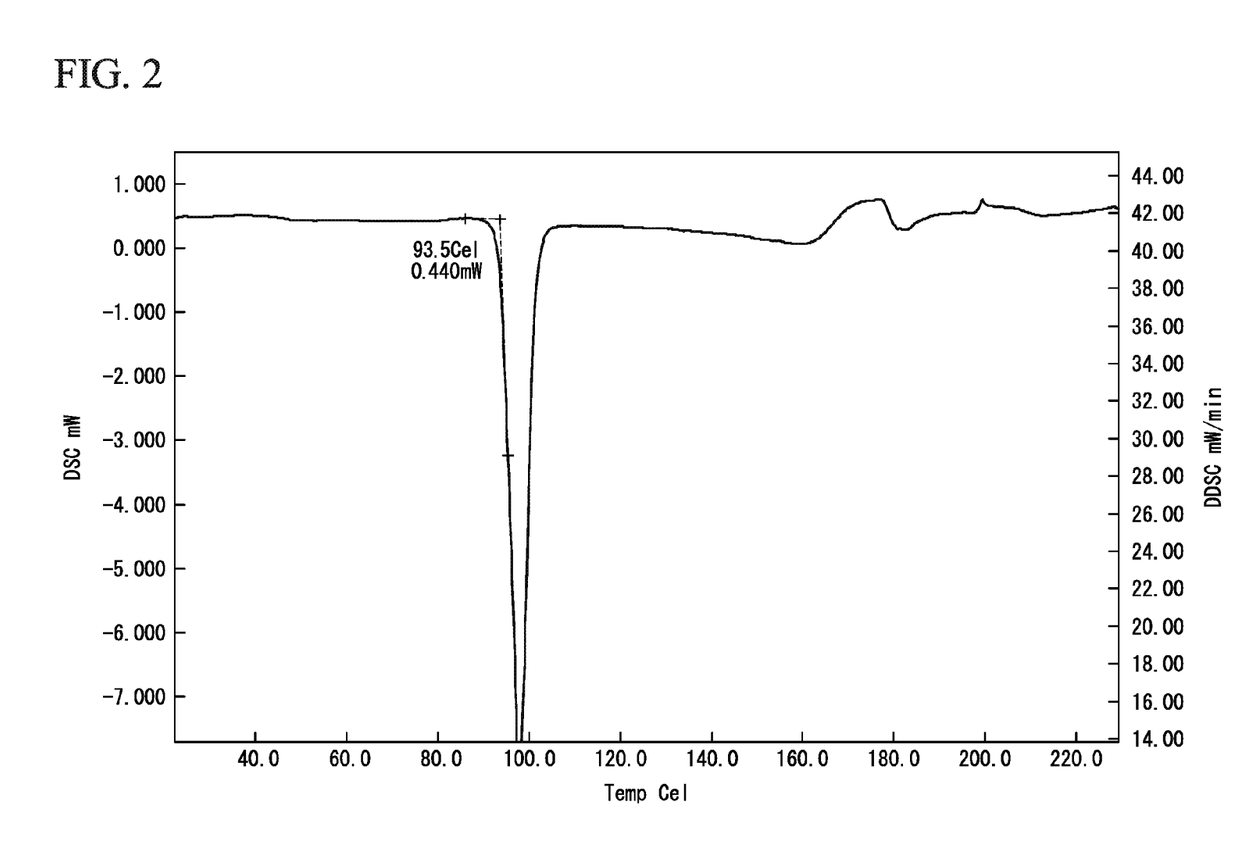
FIG. 2 is a view showing a result obtained by conducting DSC measurement of a mixture composed of acetamiprid and cyantraniliprole.

4.7 parts by mass of acetamiprid and 10 parts by mass of cyantraniliprole were dry-mixed to obtain a mixture. The mixture was subjected to DSC measurement, and the results thereof are shown in FIG. 2. The mixture composed of acetamiprid and cyantraniliprole started to melt at approximately 94° C. and exhibited behavior different from that of the co-crystal.

Example 2

10 parts by mass of acetamiprid, 21 parts by mass of cyantraniliprole, 1.0 part by mass of sodium dialkylsulfosuccinate, 4 parts by mass of polyoxyethylene glycol tristyryl phenyl ether, 0.8 parts by mass of sodium lignin sulfonate, 0.55 parts by mass of a preservative and antifoamer, and 62.7 parts by mass of water were mixed, the mixture was heated at 60° C. for 30 minutes while stirring the mixture, and then the resultant was cooled to room temperature. Then, the resultant was subjected to wet-pulverization to obtain a concentrate suspension composition A (aquatic suspended concentrate composition). The obtained concentrate suspension composition A was partially filtrated, and washed with water to obtain a crystal. The obtained crystal was subjected to DSC and XRD measurement to confirm that the spectrum of the obtained crystal was the same as that of the co-crystal obtained in Example 1.

Example 3

The concentrate suspension composition A obtained in Example 2 was diluted 4000 times with water to obtain a treatment agent (active ingredient amount in terms of acetamiprid: 25 ppm, active ingredient amount in terms of cyantraniliprole: 50 ppm).

The upper leaves of cucumbers were cut while remaining the first true leaves thereof, and the sufficient amount of the treating agent was sprayed thereon using a shoulder sprayer. The 5000-fold dilution of Rabiden 3S was used as a spreading agent. After the predetermined number of days had elapsed, three cotton aphid adults were released in each pot. The number of cotton aphid larvae was counted five days after releasing the cotton aphid adults. Each agent was sprayed on 6 pots, the pots were divided in two groups each composed of 3 pots, and the groups were exchanged at every time of releasing the insects to realize releasing the insects with a short cycle. The results are shown in Table 1.

Comparative Example 2-Comparative Example 4

Each test was conducted in the same way as that of Example 3, except that MOSPILAN (registered trademark) SP agent diluted with water (acetamiprid active ingredient amount: 25 ppm), VERIMARK (registered trademark) SC agent diluted with water (cyantraniliprole active ingredient amount: 50 ppm), or a tank mixture agent composed of MOSPILAN (registered trademark) and VERIMARK (registered trademark) (acetamiprid active ingredient amount: 25 ppm, cyantraniliprole active ingredient amount: 50 ppm) was used as a treatment agent. The results are shown in Table 1.

TABLE 1

| | Treatment agent | Control rate % 5 days after releasing insects | | | | | |
|---|---|---|---|---|---|---|---|
| | | Insect-release 3 days after spraying | Insect-release 6 days after spraying | Insect-release 11 days after spraying | Insect-release 14 days after spraying | Insect-release 19 days after spraying | Insect-release 24 days after spraying |
| Example 3 | Concentrate suspension composition A | 100 | 100 | 100 | 100 | 97.3 | 90.1 |
| Comparative Example 2 | MOSPILAN SP | 65.9 | 26.5 | 22.5 | 0 | 0 | 0 |
| Comparative Example 3 | VERIMARK SC | 100 | 98.3 | 92.1 | 93.3 | 88.4 | 38.9 |
| Comparative Example 4 | Tank mixture of MOSPILAN SP and VERIMARK SC (Amorphous) | 100 | 100 | 90.1 | 89.5 | 66.2 | 56.2 |

Control rate (%) = 100 − (Number of adult insects on treated area/Number of adult insects on untreated area) × 100

As is apparent from Table 1, the residual efficacy of the concentrate suspension composition A containing the co-crystal composed of acetamiprid and cyantraniliprole was superior to those of the single agents MOSPILAN and VERIMARK, and the tank mixture agent in which no co-crystal was formed, the active ingredient concentrations of which are the same as that of the concentrate suspension composition A, and the superiority in efficacy exhibited by forming co-crystal was confirmed.

Example 4

1 kg of rapeseeds and 40 g of the concentrate suspension composition A prepared in Example 2 were put in a plastic bag (transparent bag formed of polyethylene film), mixed to make the concentrate suspension composition A uniformly adhere to the surface of the seeds, and then the resultant was dried to obtain seeds in which 3.9 ga·i/kg seed of acetamiprid and 8.2 ga·i/kg seed of cyantraniliprole uniformly adhered to the surface of the seeds. Sieved red clay was put on a 9 cm poly pot (pot made of polyvinyl chloride) and 4 rapeseeds were seeded therein. After all the seeds had sprouted, only 3 seedlings remained. After the predetermined number of days had elapsed, three green peach aphid adults were released in each pot. In the case where leaves of the seedlings increased, approximately 1.5 leaves from the top of the seedlings remained and the lower leaves were cut to make investigation and administration easy, and the pots in which the insects were released were covered with drain nets so as to prevent escape of the insects and natural enemies attack. The number of green peach aphid larvae was counted 5 to 6 days after releasing the insects. The results are shown in Table 2.

Comparative Example 5-Comparative Example 7

Each test was conducted in the same way as that of Example 4, except that MOSPILAN (registered trademark) SP, VERIMARK (registered trademark) SC, or a tank mixture of MOSPILAN (registered trademark) and VERI- MARK (registered trademark) was used instead of the concentrate suspension composition A, and that rapeseeds in which the adhesion amount of acetamiprid was 4.0 ga·i/Kg seed, that of cyantraniliprole was 8.0 ga·i/Kg seed, or the respective adhesion amounts of acetamiprid and cyantraniliprole were independently 3.9 ga·i/Kg seed and 8.0 ga·i/Kg seed, were used. The results are shown in Table 2.

TABLE 2

| | | Control rate %5-6 days after releasing insects | | | |
|---|---|---|---|---|---|
| | Treatment agent | Insect-release 8 days after seeding | Insect-release 13 days after seeding | Insect-release 22 days after seeding | Insect-release 35 days after seeding |
| Example 4 | Concentrate suspension composition A | 100 | 90.3 | 95.9 | 86.4 |
| Comparative Example 5 | MOSPILAN SP | 100 | 95.7 | 71.4 | 57.8 |
| Comparative Example 6 | VERIMARK SC | 54.4 | 22.6 | 44.9 | 68.7 |
| Comparative Example 7 | Tank mixture of MOSPILAN SP and VERIMARK SC (Amorphous) | 100 | 89.2 | 67.3 | 57.1 |

Control rate (%) = 100 − (Number of adult insects on treated area/Number of adult insects on untreated area) × 100

As is apparent from Table 2, in the case where the seeds treated with the concentrate suspension composition A containing the co-crystal were used, high efficacy on green peach aphids was confirmed even when the insects were released 35 days after seeding, the efficacy being superior to that of MOSPILAN SP, VERIMARK SC, or the tank mixture of MOSPILAN SP and VERIMARK SC (amorphous).

Example 5

1 kg of corn seeds and 7 g of the concentrate suspension composition A prepared in Example 2 were put in a plastic bag, mixed to make the concentrate suspension composition A uniformly adhere to the surface of the seeds, and then the resultant was dried to obtain seeds in which 0.6 ga·i/kg seed of acetamiprid and 1.4 ga·i/kg seed of cyantraniliprole uniformly adhered to the surface of the seeds.

In the same manner, 1 kg of corn seeds and 21 g of the concentrate suspension composition A prepared in Example 2 were put in a plastic bag, mixed to make the concentrate suspension composition A uniformly adhere to the surface of the seeds, and then the resultant was dried to obtain seeds in which 1.9 ga·i/kg seed of acetamiprid and 4.0 ga·i/kg seed of cyantraniliprole uniformly adhered to the surface of the seeds.

A cotton wool pad and a filter paper were put in a cherry cup (cup made of transparent resin) having an opening of 90 mm, and 20 ml of tap water was poured therein. 5 corn seeds were seeded therein, a lid was put on the cup, and then the cup was left still in a temperature-controlled room (at 25° C.). After the predetermined number of days had elapsed, the number of sprouted seeds was counted, and the average germinating rate (%) was calculated. The lengths of the sprout and root of seeds sprouted 5 days after seeding were measured, and the average thereof was calculated. The results are shown Table 3.

Comparative Example 8

The test was conducted in a similar manner to that of Example 5, except that 1 kg of corn seeds was treated with MOSPILAN (registered trademark) SP in an amount of 0.7 ga·i/kg seed or 2.1 ga·i/kg seed instead of the concentrate suspension composition A, and seeds having an adhesion amount of 0.6 ga·i/kg seed or 1.9 ga·i/kg seed were used. The results are shown in Table 3.

TABLE 3

| | | | Average germinating rate (%) | | | | |
|---|---|---|---|---|---|---|---|
| | Treatment agent | Adhesion amount ga.i/kg seed | After 2 days | After 3 days | After 4 days | Sprout length (mm) | Root length (mm) |
| Example 4 | Concentrate suspension composition A | 0.6 + 1.4 (Acetamiprid + Cyantraniliprole) | 73.3 | 100 | 100 | 23.5 | 69.9 |
| | | 1.9 + 4.0 (Acetamiprid + Cyantraniliprole) | 73.3 | 93.3 | 93.3 | 20.8 | 55.5 |
| Comparative Example 8 | MOSPILAN SP | 0.6 | 40.0 | 93.3 | 93.3 | 17.4 | 43.9 |
| | | 1.9 | 0.0 | 46.7 | 60.0 | 4.0 | 15.9 |
| Control | Untreated | | 60.0 | 93.3 | 93.3 | 19.3 | 63.0 |

As is apparent from Table 3, no effects were confirmed on germination and early growth of the seeds on which the co-crystal was adhered (the seeds treated with the concentrate suspension composition A), and it was confirmed that the germinating rate, the sprout length, and the root length thereof were the same as those of untreated seeds. In contrast, a decrease in the germinating rate and poor growth of the seeds treated with MOSPILAN SP was confirmed. Thus, it is clear that early chemical damage can be reduced by forming a co-crystal.

INDUSTRIAL APPLICABILITY

A co-crystal is provided that exhibits excellent insecticidal effects over a long period of time while reducing chemical damage on useful plants. The method for industrially producing the co-crystal is also provided.

The invention claimed is:
1. A co-crystal consisting of a diamide-based insecticidal-active ingredient and a neonicotinoid-based insecticidal-active ingredient, wherein the neonicotinoid-based insecticidal-active ingredient is acetamiprid, and the diamide-based insecticidal-active ingredient is cyantraniliprole, chlorantraniliprole, or cyclaniliprole.

2. The co-crystal according to claim 1, wherein a molar ratio of the diamide-based insecticidal-active ingredient to the neonicotinoid-based insecticidal-active ingredient is 0.3 to 3.

3. A method for producing a co-crystal of claim 1, comprising: suspending a diamide-based insecticidal-active ingredient and a neonicotinoid-based insecticidal-active ingredient in a solvent to obtain a suspension; and heating and stirring the suspension.

4. The method for producing a co-crystal according to claim 3, wherein a heating temperature is higher than or equal to 40° C. but lower than or equal to a boiling point of the solvent.

5. The method for producing a co-crystal according to claim 4, wherein the heating temperature is higher than or equal to 60° C. but lower than or equal to the boiling point of the solvent.

6. The method for producing a co-crystal according to claim 3, wherein the solvent is water.

7. An agrochemical composition comprising a co-crystal of claim 1 and a surfactant.

8. A seed treatment agent comprising a co-crystal of claim 1 and water, wherein the seed treatment agent is an aquatic suspended concentrate composition.

9. A method for treating a seed, comprising: coating a seed with a seed treatment agent of claim 8.

* * * * *